United States Patent [19]
Vincze et al.

[11] Patent Number: 5,551,214
[45] Date of Patent: Sep. 3, 1996

[54] LIGACLIP LOADING MACHINE AND PROCESS

[75] Inventors: Bela Vincze, Flemington, N.J.; Alan Deeter, Thousand Oaks; Fred Dolder, Simi Valley, both of Calif.

[73] Assignee: Ethicon, Inc., Somerville, N.J.

[21] Appl. No.: 277,848

[22] Filed: Jul. 20, 1994

[51] Int. Cl.⁶ ............................ B65B 35/30
[52] U.S. Cl. .................. 53/443; 53/246; 53/250; 53/258; 53/281; 53/471; 53/475; 53/534; 53/536
[58] Field of Search .............. 29/235, 809; 59/71, 59/77; 53/143, 144, 158, 242, 243, 244, 245, 246, 249, 250, 255, 258, 281, 284.5, 443, 446, 467, 471, 473, 475, 534, 536, 542, 544

[56] References Cited

U.S. PATENT DOCUMENTS

| | | |
|---|---|---|
| 1,977,946 | 10/1934 | Kammer . |
| 2,507,883 | 5/1950 | Blackman . |
| 2,742,184 | 4/1956 | Yerkes et al. . |
| 2,855,737 | 10/1958 | Chase et al. ............... 53/245 X |
| 2,942,392 | 6/1960 | McCain et al. .............. 53/246 |
| 3,014,323 | 12/1961 | Stephen . |
| 3,068,626 | 12/1962 | Ianuzzi et al. .............. 53/246 |
| 3,093,234 | 6/1963 | Janssen ................. 53/534 x |
| 3,122,869 | 3/1964 | Miller et al. . |
| 3,286,458 | 11/1966 | Mallina . |
| 3,435,986 | 4/1969 | Brosseit . |
| 3,443,355 | 5/1969 | Birrell .................... 53/534 |
| 3,557,522 | 1/1971 | Rech ................... 53/242 X |
| 3,628,694 | 12/1971 | Nichols . |
| 3,727,371 | 4/1973 | Lorenzini et al. ........... 53/536 X |
| 3,789,575 | 2/1974 | Bross . |
| 3,862,530 | 1/1975 | Martine . |
| 3,862,536 | 1/1975 | Litchfield ................ 53/246 |
| 3,955,336 | 5/1976 | Fern et al. ............... 53/536 X |
| 4,166,466 | 9/1979 | Jarvik . |
| 4,450,839 | 5/1984 | Transue . |
| 4,454,642 | 6/1984 | Liechty ................. 29/235 X |
| 4,478,220 | 10/1984 | DiGiovanni et al. . |
| 4,491,133 | 1/1985 | Menges et al. . |
| 4,500,024 | 2/1985 | DiGiovanni et al. . |
| 4,627,215 | 12/1986 | Walz .................... 53/246 |
| 4,787,387 | 11/1988 | Burbank, III et al. . |
| 4,936,447 | 6/1990 | Peiffer . |
| 4,972,949 | 11/1990 | Peiffer . |
| 5,221,036 | 6/1993 | Takase . |
| 5,279,416 | 1/1994 | Malec et al. . |
| 5,329,749 | 7/1994 | Yamamoto et al. . |
| 5,335,481 | 8/1994 | Ward . |

*Primary Examiner*—John Sipos
*Assistant Examiner*—Daniel Moon
*Attorney, Agent, or Firm*—Emil Richard Skula

[57] ABSTRACT

An apparatus and process for loading ligating clips into ligating clip cartridges. Ligating clips are fed to an inversion wheel having cavities for receiving the clips. The clips are inverted by rotating the wheel. The clips are pushed into ligating clip cartridge covers by an insertion blade. The cartridge cover is indexed by an automatic control system to receive the clips. A cartridge base is inserted into the cover after it has been loaded with clips to form the assembled cartridge.

18 Claims, 9 Drawing Sheets

LIGACLIP LOADING MACHINE AND PROCESS

TECHNICAL FIELD

The technical field to which this invention relates is surgical ligating clips, in particular machinery and a process for loading surgical ligating clips into clip cartridges.

BACKGROUND OF THE INVENTION

Surgical ligating clips are well known in the surgical arts. The surgical ligating clips are used in surgical procedures to clip and secure various types of blood vessels. The clips are applied with conventional clip appliers. In such clip appliers, a clip is maintained between a pair of jaws which are actuated to cause the clip to be formed about a blood vessel. Conventional clip appliers can be classified as single clip appliers wherein a clip must be manually loaded into the jaws from a separate clip holding cartridge prior to each use, or multiple clip appliers wherein a clip is automatically or semiautomatically loaded into the jaws from an integral magazine prior to each use.

In order to facilitate the use of a single clip applier, manufacturers have typically packaged ligating clips in cartridges which facilitate the loading of the clips into the jaws of a clip applier. A cartridge will typically consists of a base and a cover. A plurality of clips, e.g., six, is typically contained in the cartridge in separated cavities. A clip is loaded from the cartridge into the jaws of the clip applier by inserting the jaws into an opening contained within the cover and into an underlying cavity containing a clip, and then securing a ligating clip by force fitting the clip between the jaws of the clip applier.

Ligating clip cartridges have been conventionally loaded by hand. Each ligating clip is manually loaded into an individual cavity within the cartridge. It can be appreciated that manually loading a cartridge with ligating clips is a costly, tedious and time consuming procedure. In addition, the nature of such a procedure can result in inadvertent operator error wherein the operator fails to insert a clip in each cavity of the cartridge. Therefore, what is needed in this art is an apparatus to automatically load ligating clips into ligating clip cartridges.

SUMMARY OF THE INVENTION

It is an object of the present invention to provide an apparatus and method for automatically loading ligating clips into a ligating clip cartridge.

Accordingly an apparatus for automatically loading a plurality of ligating clips into a ligating clip cartridge, wherein the cartridge comprises a base and a cover having a plurality of cavities for receiving ligating clips, is disclosed. The cartridge cover has openings in the cover in communication with the cavities. The cartridge base fits into the cartridge cover.

The apparatus has a base. A frame extends from the base. An inverting member, preferably a wheel, wheel is rotatably mounted to the frame. The inverting member has at least one ligating clip cavity for receiving at least one ligating clip. The cavity has a profile configured to receive the clips. The apparatus has an actuating mechanism, such as a gear train, for rotating and positioning the wheel. A vibrating track for feeding ligating clips into the ligating clip cavity is mounted to the frame. Also mounted to the frame is a push bar for pushing ligating clips out of the ligating clip cavity. Mounted opposite to the push bar is a biasing bar which contacts each ligating clip as it is pushed out of the cavity by the push bar and applies a biasing force opposed to the force applied by the push bar. A comb member is mounted to a slide plate. The comb has a plurality of tooth members for receiving ligating clips. The slide plate is slidably mounted to slide bars which are mounted to the base of the apparatus. The slide plate is connected to a nut which is mounted to a screw. The screw is coupled to a drive motor. The screw, nut and drive motor form an indexing mechanism for positioning the cartridge cover and comb to receive ligating clips and the cartridge base. An actuating mechanism, such as a pneumatic cylinder and piston rod, moves the comb means into a cartridge cover. A blade for pushing a ligating clip into the comb means and cavities of the ligating clip cartridge cover is mounted to the frame adjacent to the inverting member. Another actuating mechanism mounted to the frame actuates the blade. Yet another actuating mechanism mounted to the frame actuates a nest member which pushes a base into the cover while the comb is moved out of the cover, thereby completing the assembly of the cartridge. Vibrating tracks are mounted to the frame for feeding cartridge bases to the nest member and cartridge covers to the comb member.

Another aspect of the present invention is a method of loading ligating clips into a cartridge using the above-described apparatus. In the method of the present invention, ligating clips having legs connected at a central apex are fed from a vibrating hopper to a first in-line track such that the apex is pointing up. The track is vibrated to move the clips to a rotatable inverting member, preferably a wheel, having at least one ligating clip cavity for receiving a plurality of clips, wherein the ligating clip cavity has a profile for receiving the clips. A plurality of clips is loaded into the cavity. The inverting member is rotated about 180° such that the apex of each clip in the cavity is pointing down. A ligating clip cartridge cover, having a plurality of cavities for receiving ligating clips and holes through the cover in communication with the cavities, is then loaded in the following manner. A comb means is inserted through the holes in the cover and into the cavities. The comb means and cover are indexed to receive the ligating clips from the cavity in the wheel. Then, the clips are displaced out the cavity against a biasing force. Blade means are then used to push each clip perpendicularly with respect to the axis of the wheel into both the cavities in the cover and the comb means. A base is then inserted into the cover as the comb means is withdrawn.

The foregoing and other features and advantages of the present invention will become more apparent from the following description and accompanying drawings.

BEST MODE FOR CARRYING OUT THE INVENTION

The apparatus 10 of the present invention is illustrated in FIGS. 1 and 5–12. The apparatus 10 is utilized to load ligating clips 2 into a ligating clip cartridge 290. The apparatus 10 also assembles the cartridge 290.

Figure 1:
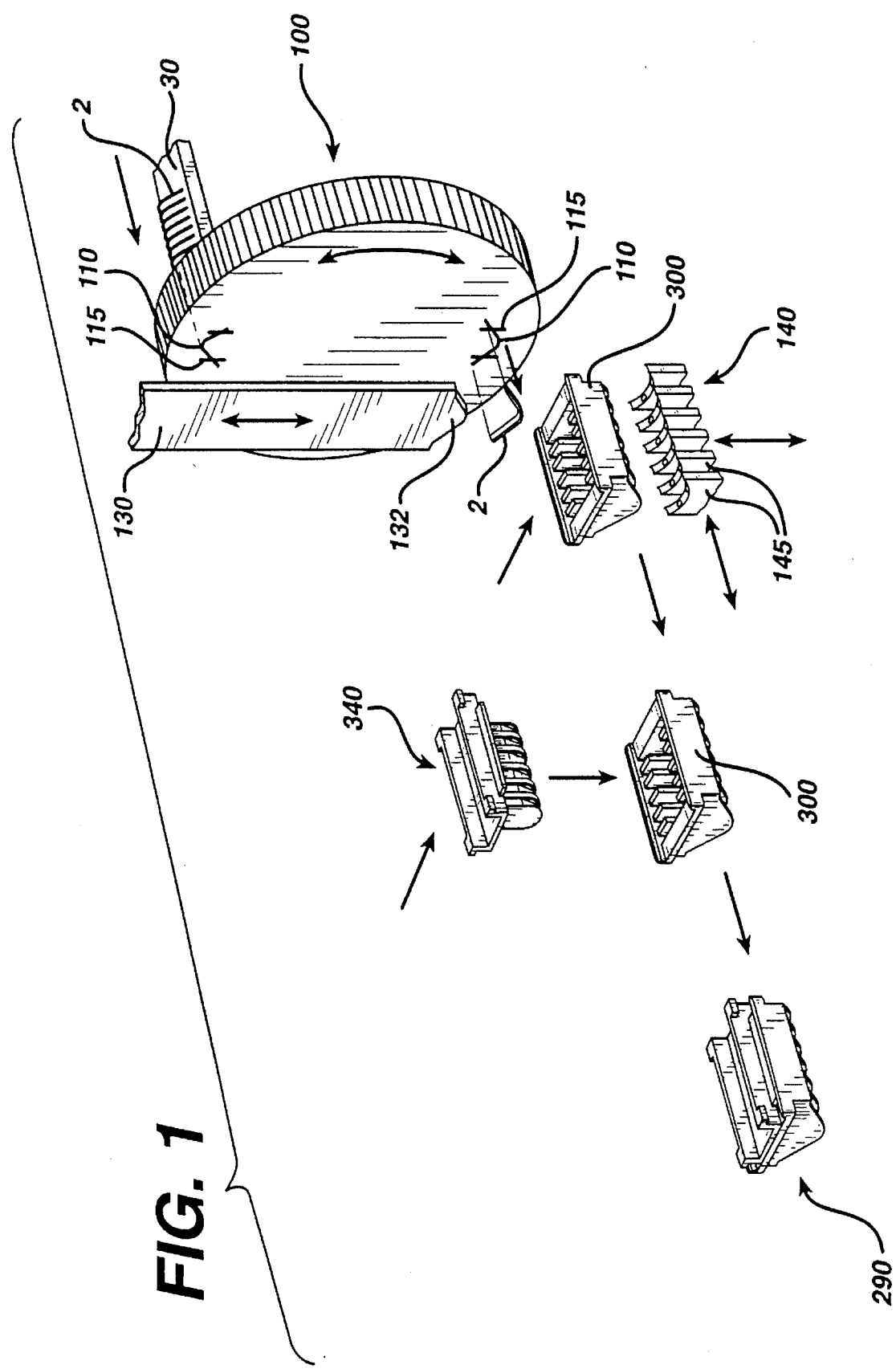
FIG. 1 illustrates a partial perspective view of the apparatus of the present invention illustrating the inverting wheel and insertion blade.
Figure 2:
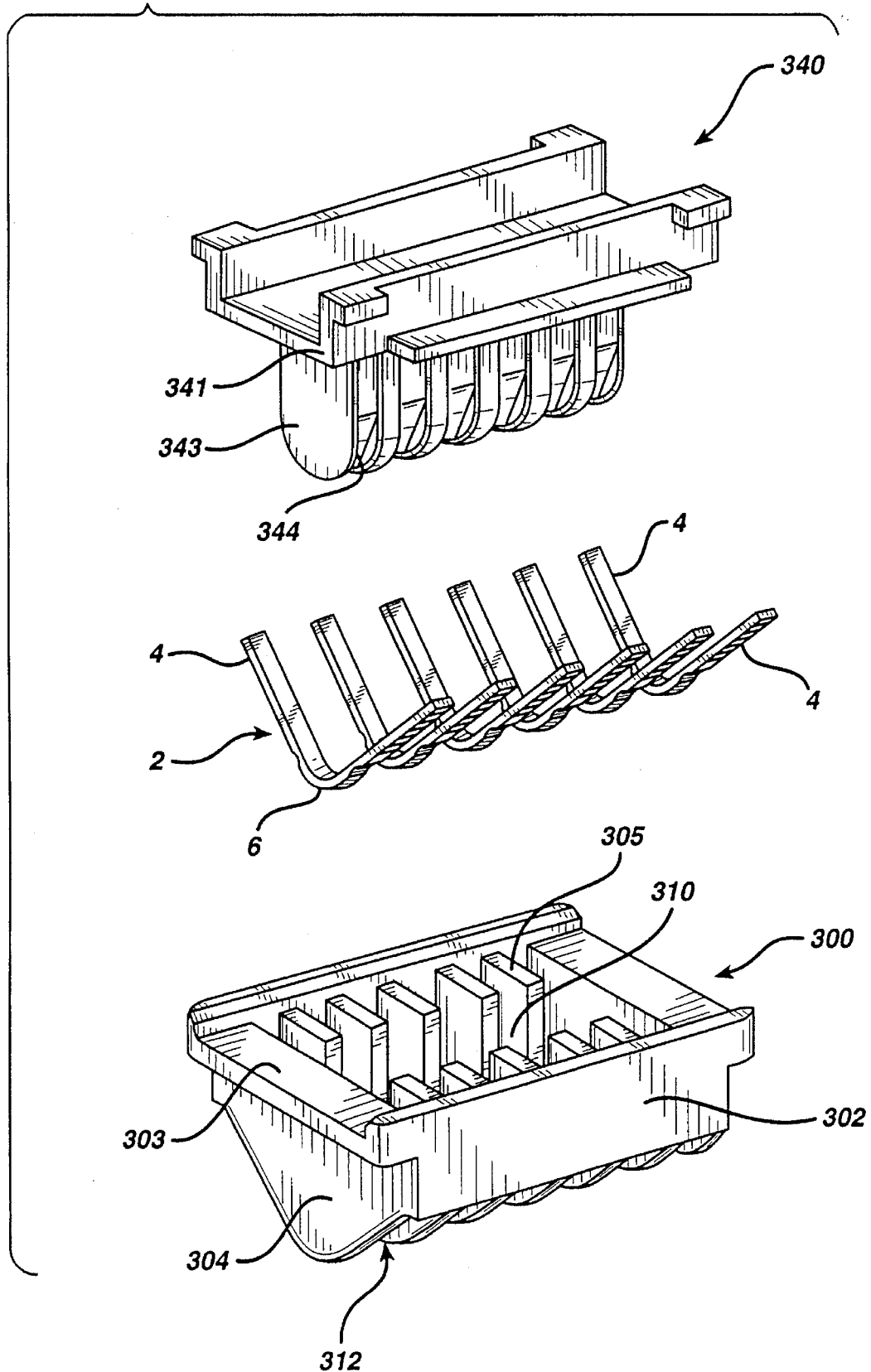
FIG. 2 is an exploded perspective view of a ligating clip cartridge and ligating clips utilized in the process of the present invention illustrating the relative positions of the cartridge base, cartridge cover and ligating clips contained therein.
Figure 3:
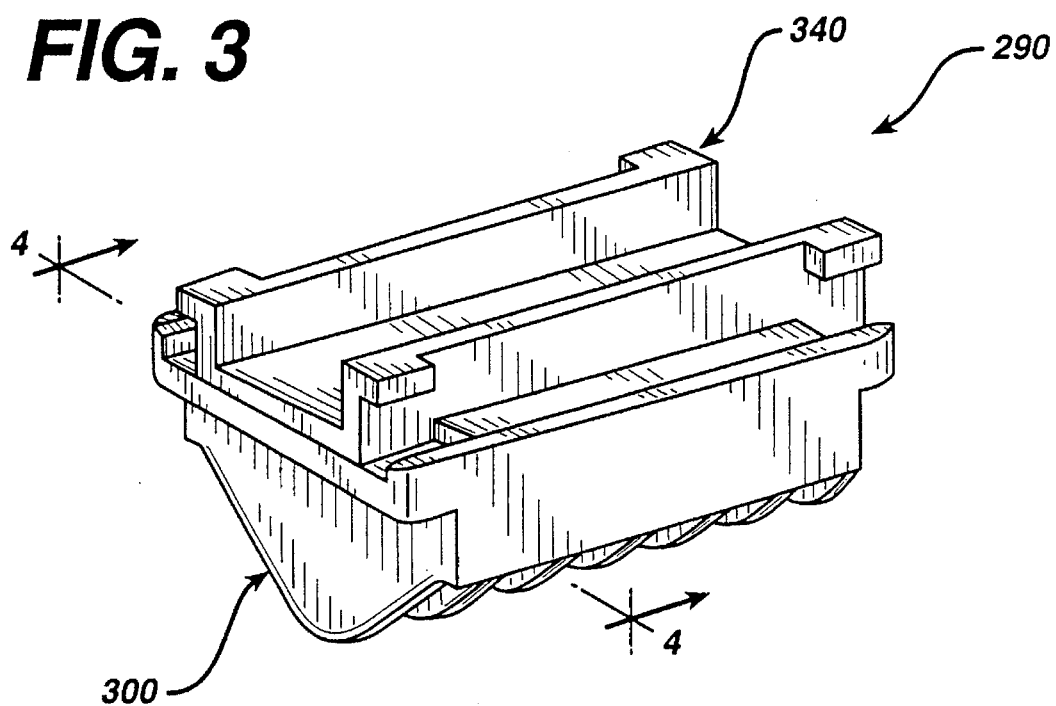
FIG. 3 is a perspective view of an assembled ligating clip cartridge.
Figure 4:
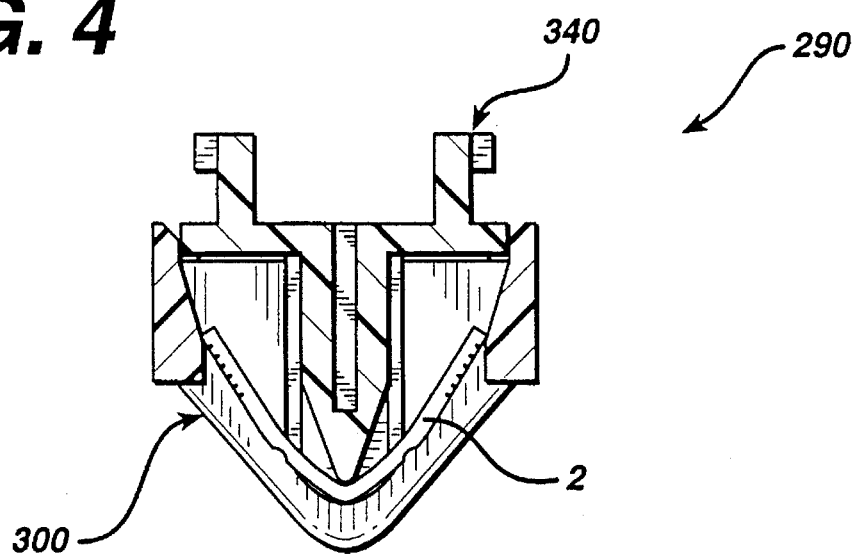
FIG. 4 is a cross-sectional view along View Line 4—4 of the ligating clip cartridge of FIG. 3.

Referring to FIGS. 2–4, the cartridge 290 is seen to consist of a base 340 and a cover 300. The cover 300 is seen to have a plurality of cavities 310 for receiving ligating clips 2. Access holes 312 through the top of cover 300 are in communication with each cavity 310. Ligating clip cartridges are know in the art, e.g., U.S. Pat. No. 3,713,533 which is incorporated by reference. Ligating cartridges typically will have a plurality of cavities for receiving the ligating clips and access holes in communication with the cavities through which the jaws of a ligating clip applier are inserted to load ligating clips.

Referring to FIG. 2, the ligating clips of the present invention are seen to have a pair of legs 4 joined at an apex 6. The legs 4 are angulated with respect to each other. The cartridge 290, as previously described, is seen to consist of a cartridge base with 340 and a cartridge cover 300.

The cartridge cover 300 is seen to have a pair of opposed triangularly shaped end pieces 304. The cover 300 is seen to have a substantially rectangular frame having a pair of opposed major sides 302 connected by a pair of opposed minor sides 303. A plurality of rib members 305 extending from the interior of the major sides 302 form cavities 310 for receiving ligating clips 2. Openings 312 at the top of each cavity 310 are in communication with the cavities 310.

The cartridge base 340 is seen to have a rectangular frame 341. Extending from the top of the rectangular frame 341 is the member 343. The member 343 has grooves 344 corresponding to the cavities 310 such that when the cartridge 290 is assembled by inserting the base 340 into the cover 300, the ligating clips 2 are each contained with the cavities 310 and the grooves 344.

Figure 5:
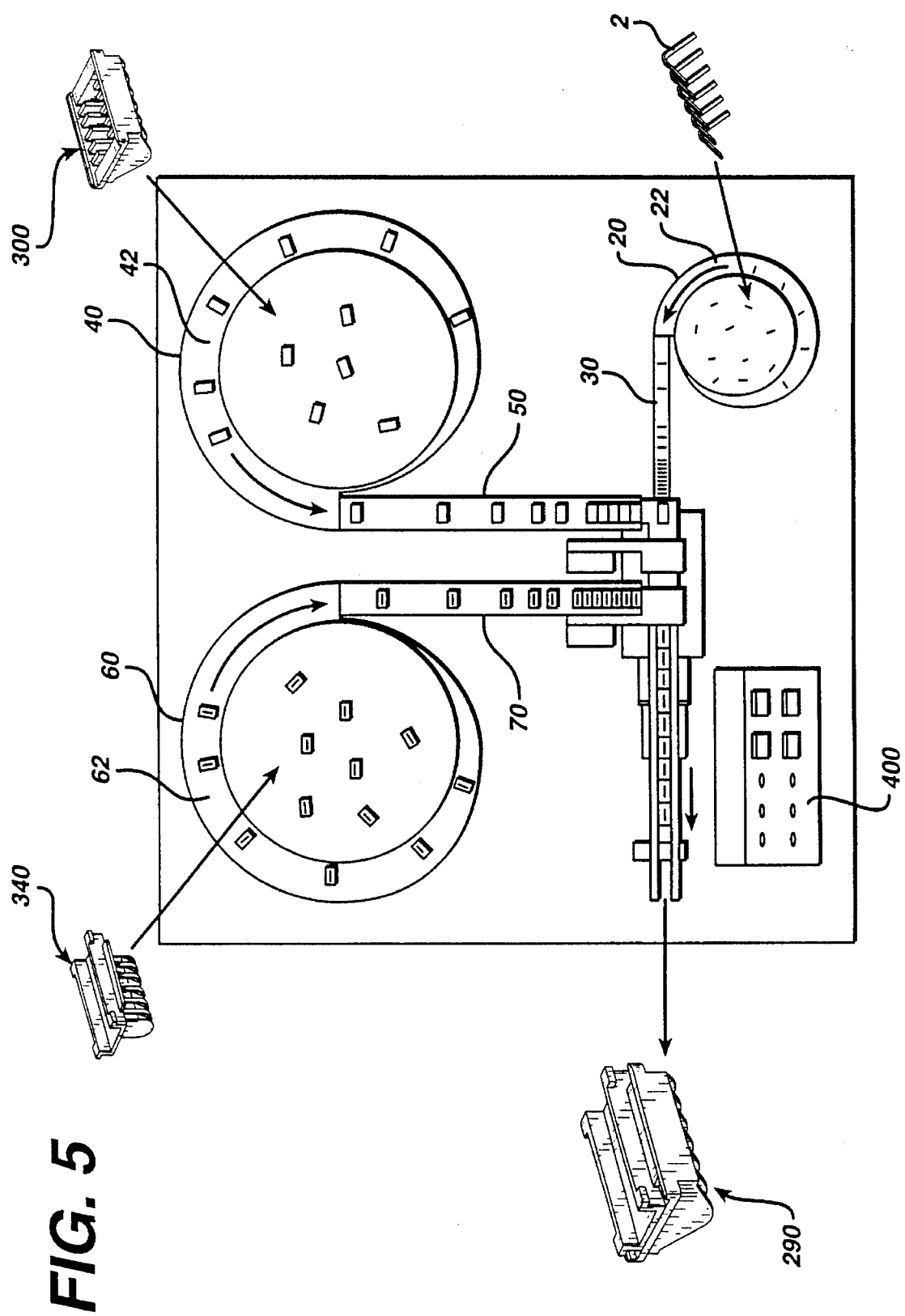
FIG. 5 is a top view of the ligating clip loading apparatus of the present invention; also illustrated are magnified perspective views of an assembled cartridge, a cartridge cover, a cartridge base and ligating clips.
Figure 6:
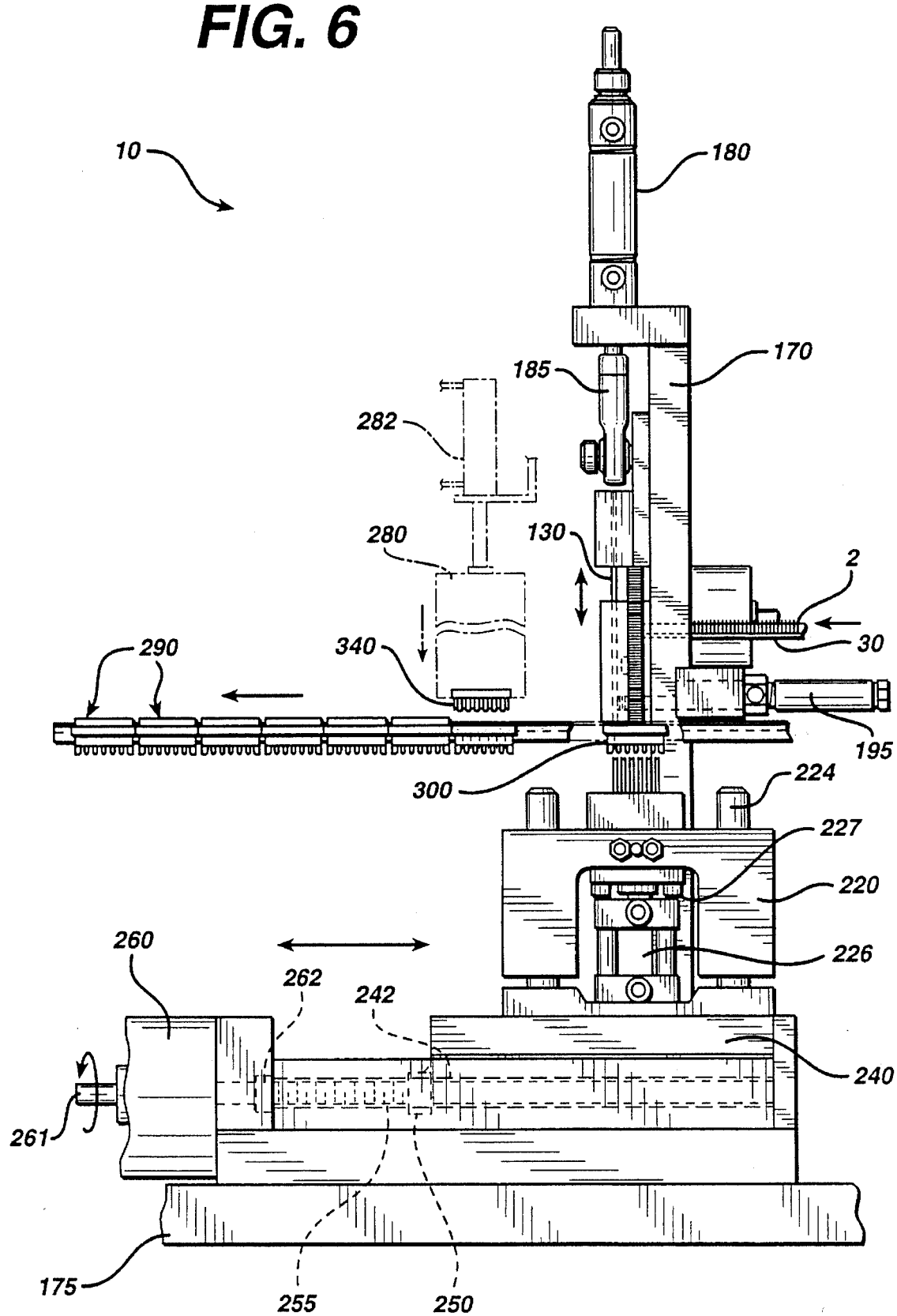
FIG. 6 is a front view of the ligating clip loading apparatus of FIG. 5.
Figure 7:
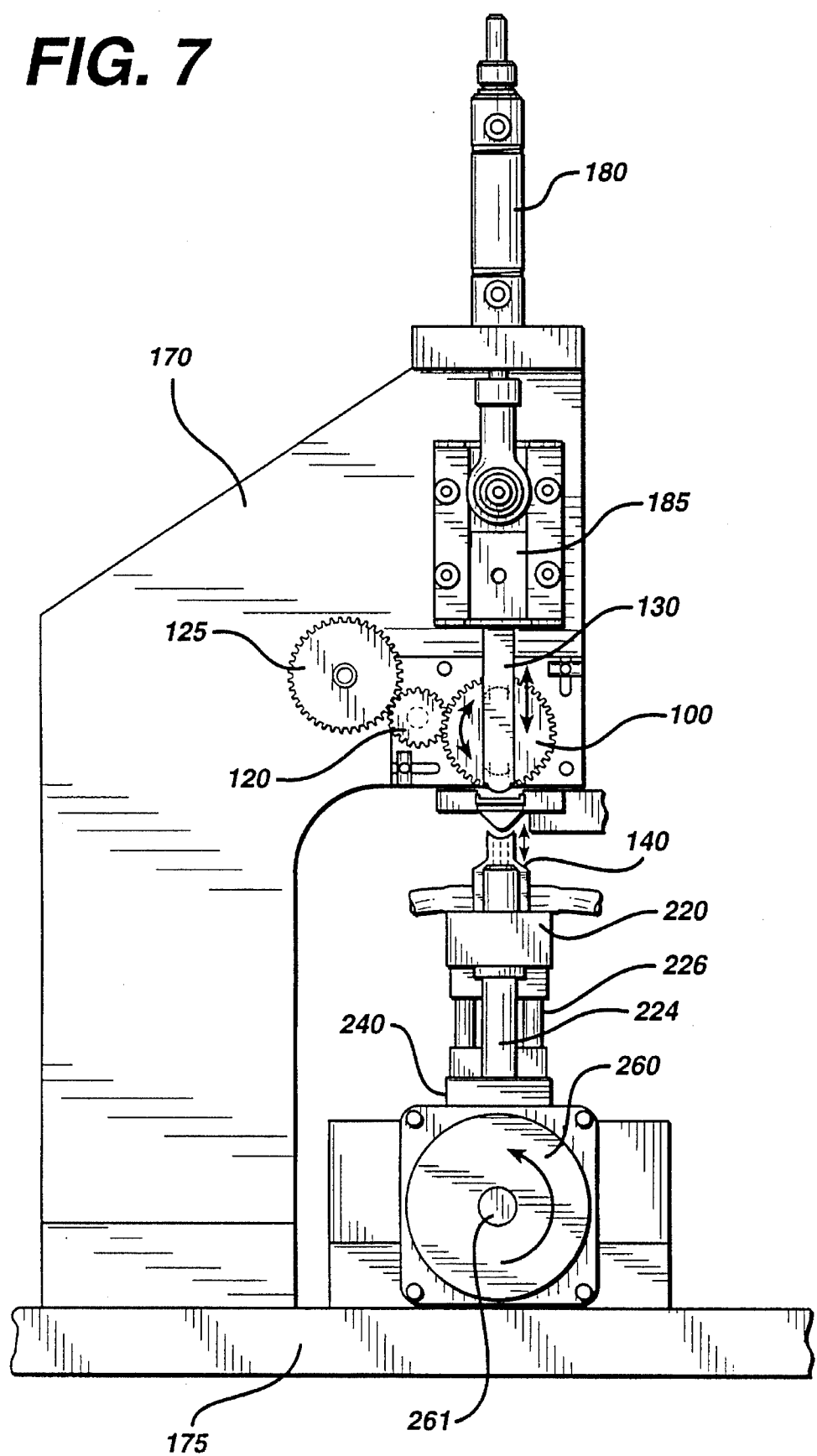
FIG. 7 is a side view of the ligating clip loading apparatus of FIG. 5.
Figure 8:
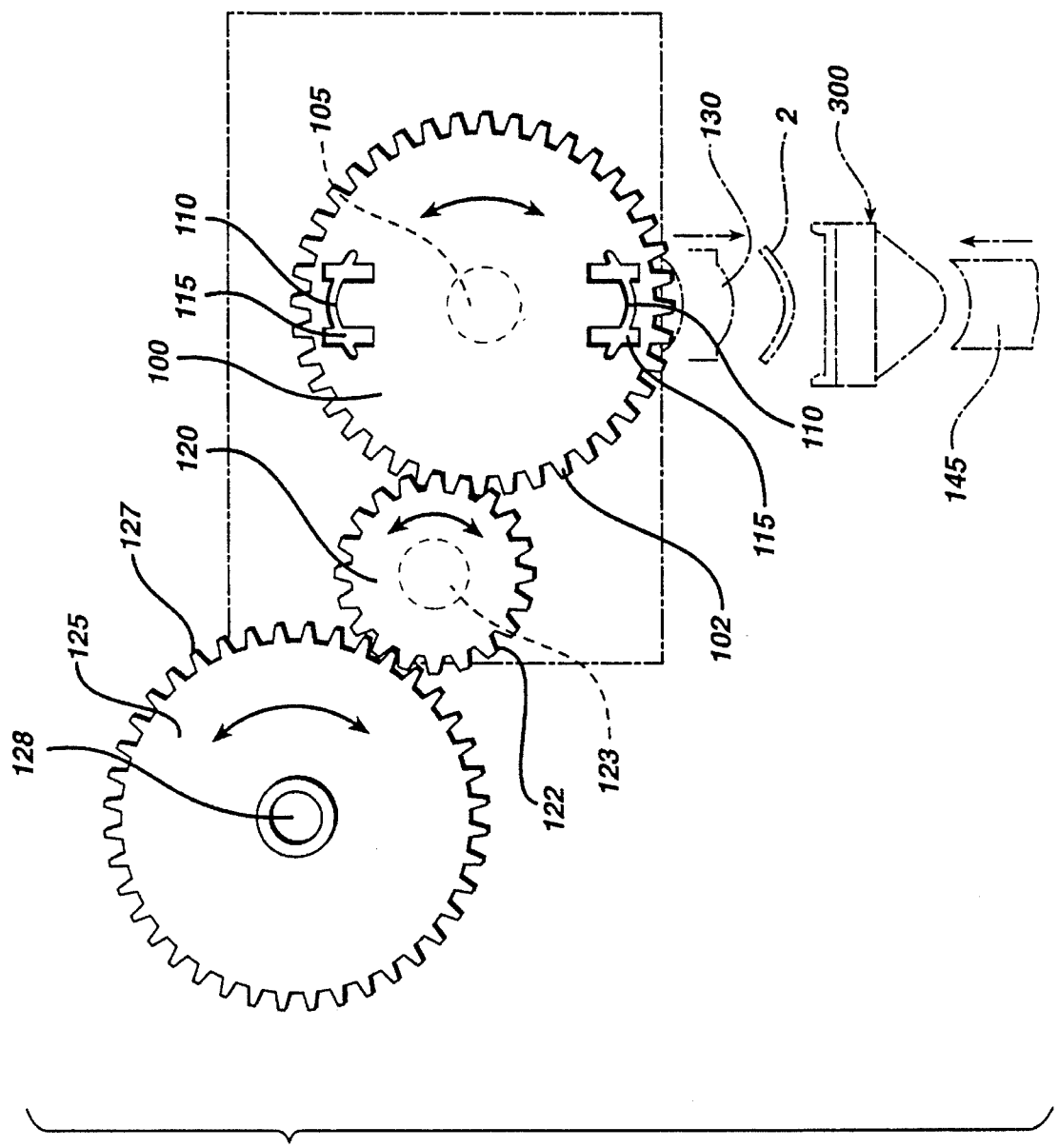
FIG. 8 is a side view of the inverting wheel and associated drive mechanism used in the apparatus of the present invention.

The apparatus 10 of the present invention as illustrated in FIG. 5 is seen to consist of a first vibratory bowl 20 connected to a track 30. Vibratory bowl 20 contains ligating clips 2. Vibratory bowl 20 is a conventional vibratory bowl feed apparatus wherein controlled vibration of the bowl 20 causes clips to translate up the spiral ramp 22 to the conventional track 30. Track 30 is also vibrated to move the ligating clips to the inverting wheel 100. The apparatus 10 also has a second conventional vibrating bowl 40 to feed covers 300 up a spiral ramp 42 to a conventional track 50. A third conventional vibrating bowl 60 feeds bases 340 up a spiral ramp 342 to a conventional track 70. Tracks 50 and 70 are also vibrated.

Referring now to FIGS. 1, and 5–12, the apparatus 10 is seen to have a support frame 170 extending from a base 175. Mounted to a shaft 105 which is rotatably mounted in the frame 170 is the inverting wheel 100. The inverting wheel 100 is seen to be a circular disk member having a plurality of external gear teeth 102. The wheel 100 is seen to have diagonally opposed, transverse, clip-shaped cavities 115. Intersecting the cavities 110 are a pair of rectangular pusher bar cavities 115 for receiving the push bars 190. The idler gear 120 is seen to have gear teeth 122 and shaft 123 which is rotatably mounted in the frame 170. The drive gear 125 is seen to have teeth 127. The drive gear 125 is rotatably mounted to frame 170. The drive gear 125 engages the idler gear 120 which in turn engages the inverting wheel 100. The drive gear is powered by a conventional motor, e.g., electric, pneumatic, etc. The gear teeth on the inverting wheel also allow the wheel to be precisely positioned for both receiving ligating clips and discharging ligating clips. Although not preferred, those skilled in the art will appreciate that the inverting wheel 100 may have other configurations including a bar-shaped member, a polyhedral member, an oval member, etc. The inverting wheel 100 may also be rotated and positioned by other conventional drive mechanism in addition to gear trains including timing chains, electronically controlled motors, indexing screw systems with stepping motors, computer controlled electromechanical systems, robotics, etc.

An insertion drive blade 130 is seen to be mounted to a drive member 135. The blade 130 is seen to have a flat, generally rectangular configuration with rounded bottom end 132. Rounded bottom end 132 has a configuration which conforms to the profile of a clip 2. Mounted to the top of frame 170 is the conventional double-acting pneumatic cylinder 180 having push rod 185. The push rod 185 is connected to the drive member 135. Drive blade 130 can move up and down. It will be appreciated by those skilled in the art that the pneumatic cylinders used in the apparatus of the present invention can be replaced by equivalent conventional actuating devices including hydraulic cylinders, solenoids, electromechanical mechanisms, cam systems, and the like and combinations thereof.

Extending from the comb support housing 220 is the comb 140. The comb 140 is seen to have teeth 145 Extending from comb base member 141. There are spaces 147 between teeth 145. The teeth 145 are spaced apart so that they can be inserted into the cavities 310 of the cover 300 to receive the ligating clips 2. The teeth 145 are seen to extend from comb base member 142. The comb support housing 220 is slidably mounted to slide members 224. The slide members 224 are preferably rod shaped members mounted to the slide base 240. Mounted to the slide base 240 between slide members 224 is the double-acting pneumatic cylinder 226 having piston rod 227. Piston rod 227 is connected to comb support housing 220 and movement of piston rod 227 causes the comb support housing 220 to move up or down on slide members 224. The slide base 240 is slidably mounted to slide bars 242 which are in turn mounted to base 175. Mounted to the slide base 240 is the nut 250 which engages the screw 255. Screw 255 is coupled to the shaft 261 of motor 260 by coupling 262. Rotation of the motor shaft 261 cause rotation of the screw 255 with resultant movement or indexing of slide base 240 and comb support housing 200 with respect to base 175. This allows the comb 140 and cartridge cover 300 to index to receive a ligating clip 2 in each cavity 310. The comb 140 and cover 300 are also indexed or moved to receive a base 340 to complete the assembly of cartridge 290. The indexing system can also utilize other conventional systems including gear trains, electronically controlled motors, equivalents thereof and the like.

Figure 9:
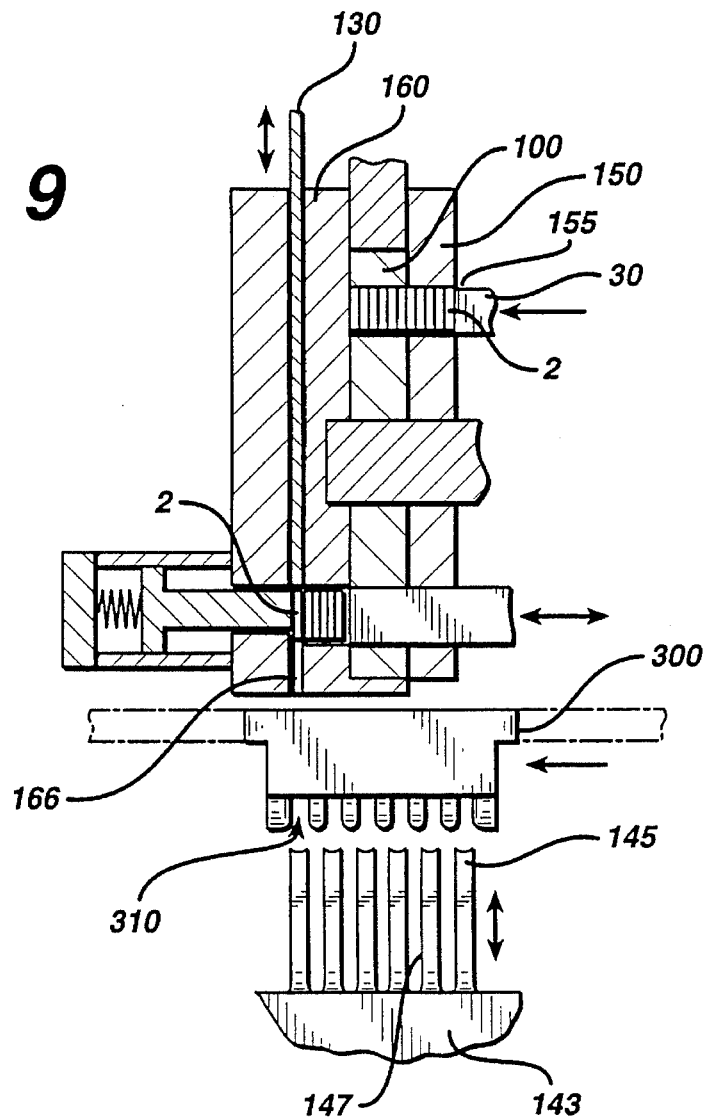
FIG. 9 is a partial cross-sectional view showing the inverting wheel and the insertion blade in relation to the loading comb and a cartridge cover.
Figure 10A:
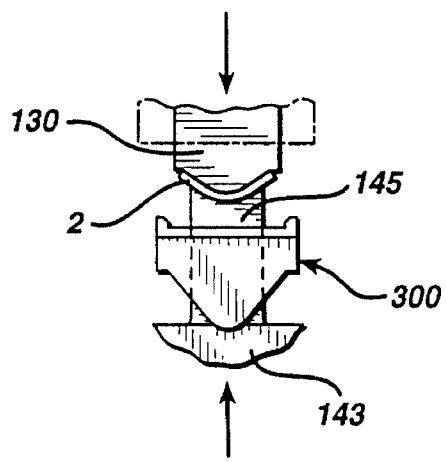
FIG. 10A is a partial side view of the insertion blade of FIG. 10 as seen along View Line 10A—10A.
Figure 10:
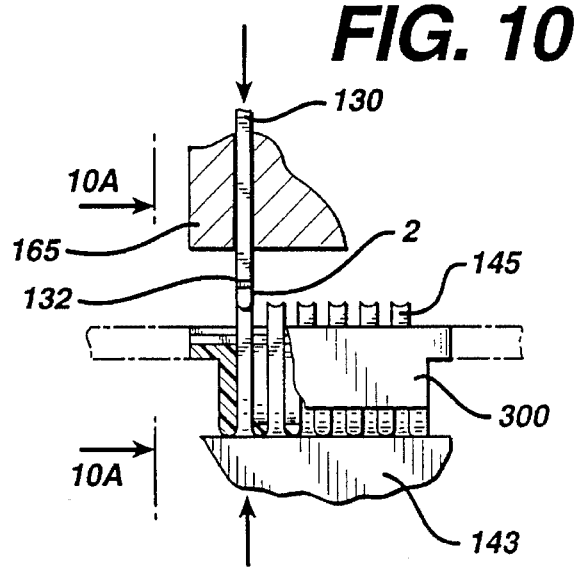
FIG. 10 is a partial, front, cross-sectional view illustrating the insertion blade pushing a ligating clip into a cavity of the cartridge cover.
Figure 11:
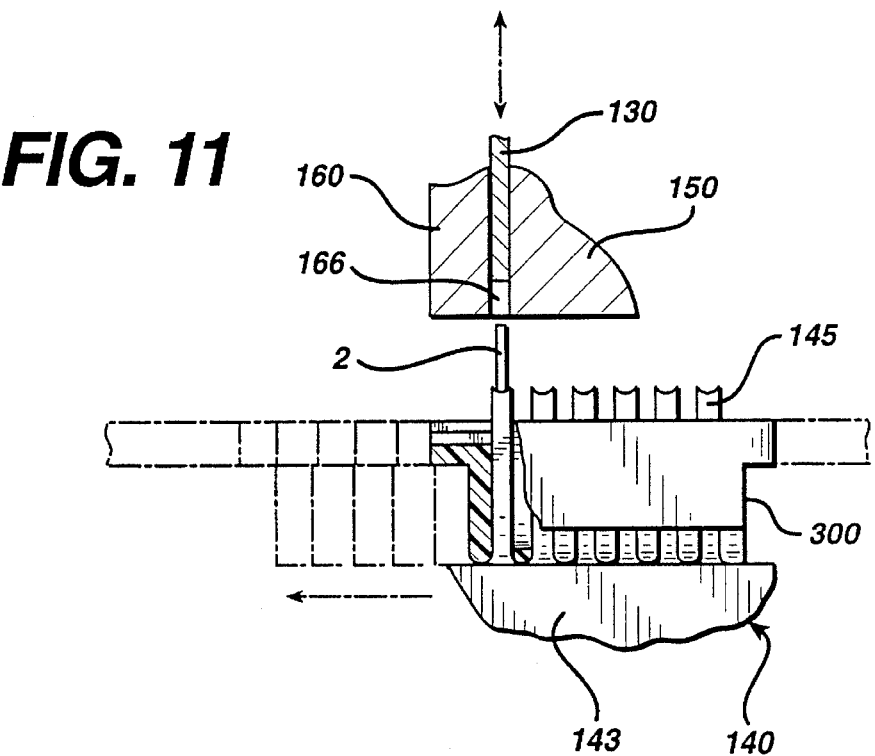
FIG. 11 is a partial cross-sectional view illustrating the insertion blade in an upward position after a ligating clip has been inserted into a cavity of the cartridge cover and also illustrating the indexing of the cartridge cover in phantom.
Figure 12:
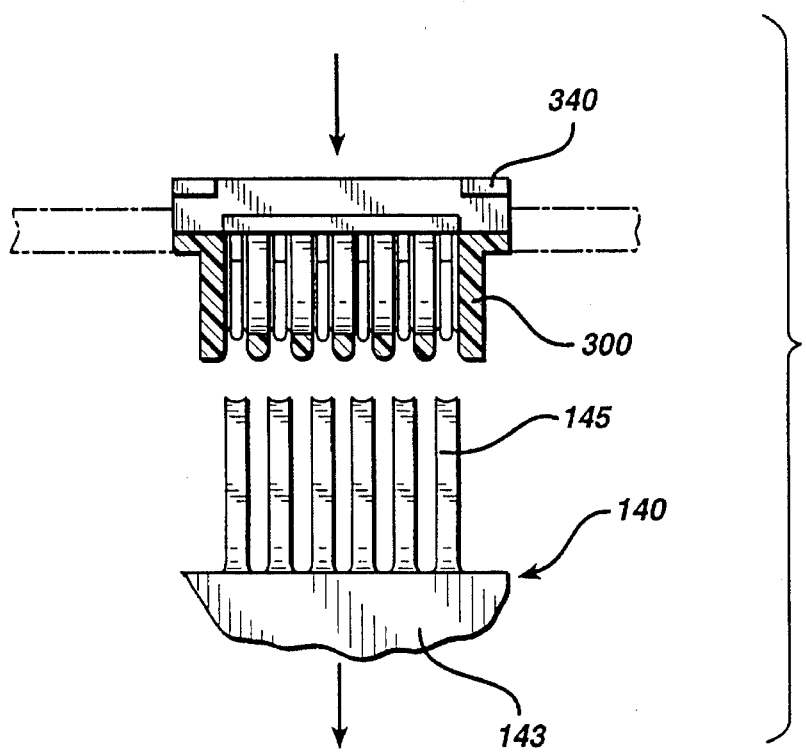
FIG. 12 is a partial front view of a loading comb after it has been moved out of the cartridge cover when the cartridge base has been inserted into the cartridge cover.

Referring to FIG. 9, the apparatus 10 is seen to have a feed plate 150, a discharge cover plate 160 and a blade cover plate 165. The plates 150, 160, and 165 are mounted to frame 170 in a stationary manner. Front cover plate 150 is seen to have upper clip-shaped opening or passage 155 for receiving clips 2 from track 30. Cover plate 150 is also seen to have lower passage 156 for receiving pusher bars 190. Discharge cover plate 160 is seen to have clip shaped-receiving cavity 162 for receiving clips 2 and pusher bars 190. Opening 155 is in alignment with a first clip-shaped cavity 105 of wheel 100 when the wheel is in the loading position, while cavity 156 is in alignment with the other clip shaped cavity 105 which is in the unloading or discharge position. Cavity 162 is in alignment with the cavity 105 of wheel 100 which is positioned in the downward, unloading position. Adjacent to discharge cover plate 160 is blade cover plate 165 having opening 167 in alignment with cavity 162. The blade cover plate is mounted adjacent to insertion blade 130 such that there is a sufficient gap forming a slot 166 for blade 130 to travel within. Discharge plate pusher bar 200 which is biased by spring 201 mounted in housing 202 extends through opening 167 into slot 166 between discharge cover plate 160 and blade cover plate 165. Housing 203 is mounted to blade cover plate 165. Blade 130 moves up and down in slot 166 and is actuated by pneumatic cylinder 180. The nest 280 is actuated by the cylinder 282 which is mounted to frame 170 via bracket 283. The nest 280 has a cavity for receiving a cartridge base 340. A vacuum is drawn on the cavity in nest 280 via a passage in communication with the cavity in order to assist in maintaining a Cartridge base 340 in the cavity. The nest 280 can be moved upwardly and downwardly by cylinder 282.

A control panel 400 for controlling the apparatus 10 is illustrated in FIG. 5. The control panel consists of conventional controls and panel displays, e.g., analog, digital, electronic, fluidic, etc. Preferably, the various systems of apparatus 10 are controlled by a conventional master computer, while individual systems may be controlled by conventional individual computers, controllers, etc.

The apparatus 10 of the present invention operates in the following manner. Clips 2 from vibrating bowl 20 are fed up ramp 22 onto track 30. The vibrating motion of track 30 moves the clips 2 through the clip-shaped opening 155 in feed plate 150 and into a clip-shaped cavity 105 of wheel 100 which is positioned in the upward position to receive clips 2. At the same time, cartridge covers 300 are fed from vibrating bowl 40 up ramp 42 to vibrating rail 50. Each cover 300 moves from vibrating rail 50 to a position over comb 140. The teeth 145 of comb 140 are inserted into the cavities 310 of the cover 300 by actuating pneumatic cylinder 226 thereby causing comb support housing 220 and comb 140 to move upwardly until the cavities 310 of cover 300 are engaged by teeth 140. A vacuum is also drawn upon the teeth 145 and the cover 130. Next, the wheel 100 is rotated 180° to move cavity 105 containing ligating clips from the upward loading position to the downward unloading position. Clip-shaped cavity 105 is now in alignment with passage 156, opening 162, and opening 167. The other, opposite empty cavity 105 is now in the upward loading position to receive clips 2. Next, the comb 140 and cover 300 are indexed by the motor 260 and screw 255 so that the first cavity 310 of the cover 300 is in alignment with the blade 130 and slot 166. This is done by rotating screw 255 a sufficient number of revolutions to effectively causes slide base 240 to move. Next, the pusher bar 190 extends through the cavities 105, 156 and 162 forces the clips 2 against the biased discharge plate pusher bar 200. The outermost clip is forced into the slot 166 contained between the discharge plate 165 and the wheel 100 and against pusher bar 190. Next, the blade 130 is moved downwardly to engage the clip 2 in the slot 166 and push it into cavity 310 and a comb tooth 145. Preferably, a sufficient vacuum is pulled on comb 140 and cover 300 to effectively maintain the clips 2 in the comb teeth 145 and cavities 310. The comb 140 and base 300 are then indexed to align succeeding cavities 310 with the slot 166 and blade 130. The process is repeated until all of the cavities are filled with ligating clips 2. After the ligating clips 2 are loaded into all of the cavities 310 of the cover 300, the cover 300 and comb 140 are indexed away from the wheel 100 and slot 166 to a base loading station. Movement of the screw 255 in the nut 250 causes the slide base 240 to move on the slide bars 242. A base 340 is fed into a receiving cavity of the nest 280 from track 70. Positioned in the bottom of the nest 280, the cavity receives the base 340. The base 340 is maintained in the nest 280 by a vacuum pulled on one or more passages in communication with the cavity of nest 280. The base 340 is then forced by an air cylinder 282 into the cover 300 (which is indexed into position by the comb 140 and side plate 240) thereby pushing the base 340 into cover 300 as the comb teeth 145 are removed out from the openings 310 and forming the cartridge 290. The fully assembled cartridge 290 then is moved by a vibrating track 210 away from apparatus 10. The comb 140 is then indexed back to an initial loading position where it receives a cover 300 as the wheel 100 is again rotated 180° and a cavity 105 containing ligating clips 2 is in the clip unloading position for discharging clips 2 into a newly positioned cover 300. The process is then repeated as the comb 140 and cover 300 are then successively indexed into place such that each cavity 310 is in alignment and indexed with the slot 166 and blade 130 to receive a ligating clip 2 and the remainder of the steps are repeated.

The novel process and apparatus of the present invention have many advantages. It is now possible to automatically load ligating clips into ligating clip cartridges in a highly automated, fast and accurate manner. The machinery is easy to use since clips, cartridge bases, and cartridge covers are simply dumped in bulk into bins and then automatically fed to the apparatus 10 and assembled.

Although this invention has been shown and described with respect to detailed embodiments thereof, it will understood by those skilled in the art that various changes in form and detail thereof may be made without departing from the spirit and scope of the claimed invention.

We claim:

1. An apparatus for loading ligating clips into a ligating clip cartridge, wherein the cartridge comprises a cover having a plurality of separated cavities for receiving ligating clips and openings in the cover in communication with the cavities, and a base which fits into the cover, the apparatus comprising:

a base;

a frame extending from the base;

an inverting member rotatably mounted to the frame, the member comprising at least one ligating clip cavity for receiving at least one ligating clip;

means for rotating the member;

means for feeding ligating clips into the ligating clip cavity, said means mounted to the frame;

means for pushing ligating clips out of the ligating clip cavity;

comb means for insertion into a ligating clip cartridge cover having cavities;

means for feeding the ligating clip cartridge cover to the comb means;

indexing means for moving the comb means and ligating clip cartridge cover into a position to receive a ligating clip in each cavity of the cartridge cover, said indexing means mounted to the base;

blade means for pushing a ligating clip onto the comb means and into cavities of the ligating clip cartridge cover;

actuating means for actuating the blade means;

means for placing a ligating clip cartridge base into the ligating clip cartridge cover, said means mounted to the frame; and, means for feeding a ligating clip cartridge base to the means for placing a ligating clip cartridge base.

2. The apparatus of claim 1 wherein the ligating clip cavities are transverse to the inverting member.

3. The apparatus of claim 1 wherein the inverting member is mounted to a shaft which is rotatably mounted to the frame.

4. The apparatus of claim 1 wherein the means for feeding the ligating clips into the ligating clip cavity comprises a vibrating track.

5. The apparatus of claim 1 wherein the comb means comprises a base having comb teeth perpendicularly mounted thereto, said comb teeth separated by spaces.

6. The apparatus of claim 1 wherein the blade means comprises a flat member having an end configured to correspond with the configuration of a ligating clip.

7. The apparatus of claim 1 wherein the means for placing the ligating clip cartridge base into the cartridge cover comprises a nest actuated by an actuating means.

8. The apparatus of claim 1 wherein the means for feeding a ligating clip cartridge base to the means for placing a ligating clip cartridge base comprises a vibrating track.

9. The apparatus of claim 1 wherein the means for feeding a ligating clip cartridge cover to the comb means comprises a vibrating track.

10. The apparatus of claim 1 wherein the actuating means for actuating the blade means comprises a pneumatic cylinder.

11. The apparatus of claim 1 wherein the means for pushing ligating clips out of the ligating clip cavity comprises a pusher bar.

12. The apparatus of claim 11 further comprising a discharge cover plate mounted to the frame and positioned adjacent to one side of the member, said plate having a passage therethrough for receiving clips and the pusher bar.

13. The apparatus of claim 1 further comprising a blade cover plate mounted to the frame and positioned adjacent to the member, the plating having a passage therethrough.

14. The apparatus of claim 13 further comprising a slidable bar mounted to the blade cover plate, said bar biased to move through the passage of the blade cover plate.

15. The apparatus of claim 1 wherein the member comprises a wheel having an outer periphery.

16. The apparatus of claim 15 wherein the wheel has gear teeth about its outer periphery.

17. The apparatus of claims 15 wherein the means for rotating the wheel comprises a gear drive.

18. A method of loading ligating clips into a cartridge, comprising:

feeding ligating clips having a central apex from a hopper to an in-line track such that the apex is pointing up;

moving the clips on the track to a rotatable member having a least one longitudinal cavity for receiving a plurality of clips, wherein the longitudinal cavity has a longitudinal axis and a profile for receiving the clips;

loading a plurality of clips into the cavity;

rotating the member about 180° such that the apex of each clip in the cavity is pointing down;

mounting a ligating clip cartridge cover onto a comb means and indexing the comb means and cover to receive the ligating clips from the wheel;

displacing the clips out of the cavity;

using blade means to push each clip perpendicular to the longitudinal axis of the cavity onto comb means;

pushing a cartridge base into the cover thereby assembling a loaded ligating clip cartridge while removing the comb means from the cover.

\* \* \* \* \*